(12) United States Patent
Mawson et al.

(10) Patent No.: US 9,700,717 B2
(45) Date of Patent: Jul. 11, 2017

(54) APPARATUS AND METHOD FOR TREATING AND PREVENTING FORMATION OF PRESSURE ULCERS

(75) Inventors: Anthony Richard Mawson, Jackson, MS (US); Robert J. Hirko, Jackson, MS (US)

(73) Assignee: Chalfont LLC, Jackson, MS (US)

( * ) Notice: Subject to any disclaimer, the term of this patent is extended or adjusted under 35 U.S.C. 154(b) by 1205 days.

(21) Appl. No.: 13/066,965

(22) Filed: Apr. 29, 2011

(65) Prior Publication Data
US 2012/0277825 A1 Nov. 1, 2012

(51) Int. Cl.
*A61H 1/00* (2006.01)
*A61N 1/20* (2006.01)
*A61N 1/36* (2006.01)

(52) U.S. Cl.
CPC .............. *A61N 1/205* (2013.01); *A61N 1/20* (2013.01); *A61N 1/36021* (2013.01)

(58) Field of Classification Search
CPC ....... A61N 1/205; A61N 1/20; A61N 1/36021
USPC ............................................................ 607/75
See application file for complete search history.

(56) References Cited

U.S. PATENT DOCUMENTS 6,397,103 B1 * 5/2002 Canali ..................... G21K 5/00
607/2

* cited by examiner

*Primary Examiner* — Christopher D Koharski
*Assistant Examiner* — Philip C Edwards (57) ABSTRACT

An apparatus and means of detecting tissue conditions conducive to pressure ulcer formation and reversing these conditions which includes the steps of: noninvasively detecting tissue parameters indicative of tissue health, calculating when these conditions fall outside normal healthy physiological ranges in such a manner that indicates future formation of a pressure ulcer, and in such a situation applying therapeutic stimulation to normalize tissue physiological condition. Said apparatus and method comprise a single, wearable unit. The device can be used in bed or in a wheelchair to treat and prevent the development of pressure ulcers.

6 Claims, 5 Drawing Sheets

APPARATUS AND METHOD FOR TREATING AND PREVENTING FORMATION OF PRESSURE ULCERS

REFERENCES CITED

U.S. PATENT DOCUMENTS

| | | |
|---|---|---|
| 4,727,878 | March 1988 | Levine |
| 6,363,284 | March 2002 | Nachum |
| 7,122,012 B2 | October 2006 | Bouton |
| 3,694,742 | September 1972 | Bergmanis |
| 5,458,626 | October 1995 | Krause |

OTHER PUBLICATIONS

Mawson, A. R., et al. "Risk Factors for Early Occuring Pressure Ulcers Following Spinal Cord Injury," American Journal of Physical Medicine and Rehabilitation, 1988; 67:123-127.

Mawson, A. R., et al. "Enhancing Host Resistance to Pressure Ulcers: A New Approach to Prevention," Preventive Medicine, 1993; 22:433-450. (a)

Mawson, A. R., et al. "Effect of High Voltage Pulsed Galvanic Stimulation on Sacral Transcutaneous Oxygen Tension Levels in the Spinal Cord Injured," Paraplegia, 1993; 31:311-319.(b)

BACKGROUND TO THE INVENTION

Field of the Invention

The present invention provides an apparatus and method for automatically 1) monitoring the skin in order to detect when tissue is at risk for developing pressure ulcers, and 2) when required, applying appropriate electrical stimulation to increase the resistance of compromised areas of tissue to the development of those ulcers. Specifically, parameters of tissue health including $SpO_2$, Perfusion Index, $P_{tc}O_2$, and others, are monitored using existing non-invasive technology. Values of these parameters are then used, individually or in concert, for computation by a specialized control unit to determine the condition of monitored tissue and its susceptibility to the development of pressure ulcers. When susceptibility is above a threshold level, high voltage pulsed galvanic stimulation is applied noninvasively to stimulate appropriate nerve roots, altering physiologic state of the tissue, increasing levels of monitored parameters into the normal range, and thereby causing the tissue to be resistant to ulcer development. The device for accomplishing this objective is housed in a single unit and can be worn by the subject while in a bed or wheelchair.

BACKGROUND

An estimated 2.5 million pressure ulcers are treated each year in the United States in acute care facilities alone, at a cost of $11 billion. The cost of treating an individual pressure ulcer usually ranges up to $40,000 but can exceed $100,000, depending on the severity of the wound. Up to 24% of persons in nursing homes reportedly have a pressure ulcer (also called bed sores and decubitus ulcers). We will use the term pressure ulcers in this application. Given their numbers and cost of treatment, pressure ulcers are an important public health issue. There is a pressing need to develop effective modes of treatment and prevention.

Defined as localized areas of cellular necrosis of the skin and subcutaneous tissues due to pathologic changes in the blood supply, pressure ulcers tend to develop on the lower parts of the body, especially in tissue above the sacrum, trochanters, and ischial tuberosities. Once considered an inevitable consequence of traumatic transverse lesions of the spinal cord, often leading to sepsis and early death, pressure ulcers remain one of the most common complications of spinal cord injury (SCI). Pressure ulcers have been reported to occur in from 28% to 85% of patients with SCI, often within a few days of injury. In addition to reducing the patient's quality of life and adding a further burden to the psychological trauma of injury, pressure ulcers are associated with significant morbidity and mortality.

Of the many factors implicated in the pathogenesis of pressure ulcers, the most important has always been considered to be localized pressure, resulting initially in impaired capillary circulation and eventually in necrosis. Hence, repositioning every 1-2 hours to avoid constant pressure has become a fundamental precept in the management of high-risk patients. Although localized pressure is a necessary factor in ulcer development in SCI, it is not considered sufficient. Consensus is growing that both intrinsic and extrinsic factors determine their formation.

The most important intrinsic factor is the loss of vasomotor control over skeletal muscles, skin and mucosa, which is greatest during the stage of spinal shock and flaccid paraplegia or quadriplegia, and results from the interruption of spinal vasomotor pathways. Since this lowers the tone of the vascular bed below the level of the lesion, externally applied pressures that would normally fail to interrupt the blood supply will result in ischemia under these circumstances. Thus, a defect in vascular control caused by autonomic dysfunction is thought to interact synergistically with ischemia due to external pressure to increase the risk of cellular damage and necrosis.

Consistent with this assumption, a prospective study of the development of pressure ulcers in a conservative series of newly admitted patients with spinal cord injury over a one year period by Mawson et al. (1988) showed that, although duration of immobilization prior to hospitalization was a significant risk factor, the factor most strongly associated with a pressure ulcer developing within 30 days of injury was low systolic blood pressure at the time of hospital admission. These findings support the notion that reduced tissue perfusion increases susceptibility to pressure ulcers.

Autonomic dysfunction in SCI tends to involve varying degrees of sympathetic loss with unopposed parasympathetic activity. Since the systemic vascular resistance is mainly a function of the sympathetic nervous system (SNS), the former drops to extremely low levels when the SNS is lost, especially in cervical cord injury. With the loss of sympathetic innervation of the heart and its chronotropic effects, varying degrees of bradycardia occur in response to the unopposed action of the vagus. Circulatory stasis and tissue hypoxia secondary to reduced vascular tone are further compounded in quadriplegia by pulmonary insufficiency.

In studies to date, various proxy measures have been used for assessing tissue oxygenation (e.g., skin blood flow or SpO2) rather than tissue oxygenation itself. In addition, little is known about tissue oxygenation as a risk factor for pressure ulcers. In a study carried out by Mawson and colleagues, sacral transcutaneous oxygen tension ($P_{tc}O_2$) levels were compared in 21 spinal cord injured and 11 able-bodied subjects lying prone and supine on egg-crate mattresses. It was found that the SCI subjects had significantly lower $P_{tc}O_2$ levels than the controls in the prone position, and markedly lower levels in the supine position, which also remained low, while those of able-bodied controls returned to the prone level. Furthermore, half (50%) of those below the median supine $P_{tc}O_2$ level (60 mmHg) had a sacral pressure ulcer compared to only nine percent (9%) above the median. The usual two-hourly repositioning schedule may therefore be insufficient to prevent pressure ulcers in the spinal cord injured.

Present methods to reduce the risk of pressure ulcers focus on ways of reducing external pressure through frequent repositioning and the use of special pressure-relieving devices such as inflatable mattresses and oscillatory beds. However, such efforts are only partially effective at best, judging by the current magnitude of the problem. In addition, frequent turning is not always desirable or practicable and can be extremely costly. Persons with SCI are immediately at risk of developing pressure ulcers after their injury, but turning is inadvisable before neurological assessment. In fact, SCI patients often cannot be repositioned during the early post-injury phase, due to spinal or vasomotor instability, thereby virtually guaranteeing a pressure ulcer. The act of turning itself is also difficult and time-consuming for caregivers.

The requirement that patients should be repositioned every two hours, day and night, is a demand that few hospitals or nursing units can meet. Patients lying on their side or in a seated position need to be repositioned every hour, and current therapy practice recommends a 2 minute pressure release every hour for SCI patients with no evidence of developing pressure ulcers. If conditions indicate imminent pressure ulcer formation, pressure release is indicated for 2 minutes every 30 minutes. However, sufficient nursing staff are seldom available to comply with these requirements. Finally, pressure-relieving mattresses and oscillatory beds, in particular, are costly and not usually available for all patients at risk. In view of these limitations, it would be desirable to have an auxiliary means of prevention that does not involve pressure relief or turning.

Based on the above review of etiologic factors, pressure ulcers might be prevented, in theory, not only by reducing external pressure but also by increasing the patient's resistance to pressure; that is, by directly influencing vascular tone in the area of interest, peripheral circulation, and as a result, tissue oxygenation. As noted, evidence is mounting that persons with SCI may be at increased risk of pressure ulcers not only due to prolonged immobilization but also to the injury-induced loss of sympathetic tone and decreased vascular resistance, which decreases the perfusion pressure gradient in the capillary beds.

There is evidence that electrical stimulation applied directly across the injury increases cutaneous blood flow in SCI and promotes the healing of pressure ulcers. In an alternative approach it was demonstrated by Mawson and colleagues that high voltage pulsed galvanic stimulation (HVPGS) could restore sympathetic tone below the level of the lesion, thereby increasing the perfusion pressure gradient and reducing the risk of pressure ulcers. They demonstrated that HVPGS, applied to the back at spinal level T5, can increase sacral transcutaneous oxygen tension levels in SCI subjects into the normal range.

It is, therefore, the object of this invention to provide a means of treating pressure ulcers and also of preventing incipient pressure ulcers. Monitoring the typically low sacral tissue $SpO_2$, Perfusion Index, and $PO_2$ levels of patients with spinal cord injury (and other patients at high risk of pressure ulcers) and maintaining them within the normal range. The method involves transcutaneously monitoring physiologic parameters of tissue state at the sacrum or other at-risk tissue and applying high voltage pulsed galvanic stimulation to increase these levels when they fall below a set point. A subsidiary object of the invention is to provide a means of maintaining the typically low sacral $P_{tc}O_2$ levels in the spinal cord injured and others at risk of developing pressure ulcers.

PRIOR ART

There is only one previous U.S. patent dealing with the use of electrical stimulation for the prevention of pressure ulcers (Inventor: Simon Levine, U.S. Pat. No. 4,727,878; Mar. 1, 1988). In Levine's patent, percutaneous electrical stimulation is used to inhibit the formation of pressure ulcers by (a) inducing by muscular contractions and hence pressure variations by causing undulations in the tissue, and (b) increasing muscle blood flow: Although Levine has not demonstrated that electrical stimulation prevents pressure ulcers, he has shown that direct stimulation of the gluteus maximus muscle increases muscle blood flow, as measured by Xenon clearance.

The present application differs from that of Levine in several major respects. First, electrical stimulation from this device is not intended to stimulate muscle directly—whether to cause tissue undulations or to increase muscle blood flow—but to activate the peripheral sympathetic nervous system, thereby increasing the capillary perfusion gradient (Mawson et al., 1993a). Secondly, rather than monitoring blood flow, the present application focuses on monitoring tissue health as measured by a combination of transcutaneous SpO2, perfusion index, oxygen tension ($P_{tc}O_2$), edema, electrical permittivity, and others, as necessary. Thirdly, in the present application, a method is described for treating and preventing pressure ulcers in which a tissue-monitoring function and electrical stimulation are combined in a biosensor-driven device in which electrical stimulation is administered automatically, depending on the state of tissue perfusion, oxygenation, and/or permittivity.

Numerous devices have been and continue to be marketed that utilize electrical currents for the purpose of stimulating and increasing the healing rate of existing open wounds. One such patent is that of Zvi Nachum, U.S. Pat. No. 6,363,284 B1; Mar. 26, 2002. This patent, and similar techniques, are focused on specific electrical stimulation at the wound site aimed at increasing the healing rate of existing pressure ulcers and other open wounds. Another is that of Horst Krause, U.S. Pat. No. 5,458,626; Oct. 17, 1995. This patent uses electrical stimulus in sync with identical periods of sequential cardiac cycles.

Monitoring of electrical parameters of tissue, which are dependent upon state of the tissue, has been shown by numerous patents as well. Two representative examples are shown by Buton et al., U.S. Pat. No. 7,122,012 B2; Oct. 17, 2006, and Bergmanis et al., U.S. Pat. No. 3,694,742; Sep. 26, 1972 illustrate the range of such electrical parameter measurement.

SUMMARY OF THE INVENTION

The present invention overcomes limitations encountered in the prior art for treating pressure ulcers by detecting conditions conducive to the formation of ulcers before they are fully developed, and takes positive measures to reverse those conditions. Circulatory stasis and tissue hypoxia secondary to reduced vascular tone are the key conditions that this device detects and reverses prior to the progression of tissue into a necrotic state. Steps toward that state are currently viewed as follows.

SCI begins the process by interrupting sympathetic innervation of smooth muscle in affected vascular beds. It is well known that loss of this innervation causes loss of vasomotor tone, resulting in a marked decrease in arterial pressure in the affected vascular beds. Lower arterial pressure ultimately leads to alteration of fluid balance and gas transport in the tissues, lowering pO2, increasing pCO2, and decreasing cellular metabolite removal from the affected bed through fluid leakage into the interstitial compartment. Vasomotor stasis results in a decreasing spiral of the cellular environment toward a state where normal life processes are not viable and necrosis occurs. This process of cellular necrosis is facilitated and compounded by external pressure applied to tissue over bony prominences, which causes ischemic injury.

The present invention interrupts this process early on to prevent the inevitable terminal outcome. It is contained in a wearable vest which includes all components. By monitoring large areas of tissue in susceptible areas, the oxygenation state and vascular viability are deduced. This is performed by monitoring several factors which may include, among others Perfusion Index, Oxygen Saturation, $P_{tc}O_2$, $P_{tc}CO_2$, tissue permittivity, or conductivity. Sensor arrays in the vest permit larger areas of tissue to be monitored than are covered by conventional clinical monitors. With appropriate embodiments the whole sacral area may be covered.

Values of the monitored parameters are used by a controller to determine the instantaneous state of the monitored tissue bed. When the measured conditions meet those determined as a threshold for imminent formation of a pressure ulcer, actions are taken by the controller to change the state of vasomotor tone in the tissue bed. This is was demonstrated in principle in earlier experiments by Mawson et al. (1993a,b), showing that electrical stimulation applied to the back at thoracic levels T5-6 in patients with spinal cord injury could raise transcutaneous oxygen tension levels at the sacrum into the normal range within a few minutes. In the proposed device for treating and preventing pressure ulcers, when appropriately placed electrodes housed in a vest-like garment are activated by signals of reduced tissue vital state at the sacrum or other at-risk areas, and electrical stimulation is automatically activated which causes the perfusion level in the affected area to rise into the desired range.

Monitoring of the skin is continuous, thereby permitting the controller to cease applying stimulation when tissue parameters are again above the minimum level. This process is repeated if and when the monitored tissue bed falls below a setpoint.

The invention is contained in a wearable appliance that can be used by an individual while seated or lying either prone or supine.

DETAILED DESCRIPTION OF THE INVENTION

Many of the sensing techniques utilized in this invention exist and frequently serve as data for medical personnel. Stimulus devices utilized in this invention also exist and are used by medical personnel for therapeutic purposes. This is the first time, however, that these devices have been combined in such a way as to sense tissue breakdown and act to reverse and prevent such breakdown.

Tissue breakdown occurs at the cellular level when energy is lacking to maintain chemical processes and gradients across cell membranes and compartment boundaries. What begins this process in most cases is not completely understood, but lack of delivery of oxygen and other nutrients to the cells, and lack of removal of waste metabolic byproducts from the cell environment are key factors. Any one or a combination of these factors can initiate the process of tissue degradation, the final result of which is necrotic tissue damage and an ulcerated area. For example, if capillary bed circulation is compromised, oxygen levels decline, cellular processes are compromised, structure of cells degrades, cells swell and may burst, capillary permeability to fluids increases, fluid exudes into interstitial space further compromising capillary flow, and the process snowballs.

Evidence of this process can be sensed on the macroscopic level in a tissue bed by monitoring one or a combination of the following parameters:

partial pressure of dissolved Oxygen, $PO_2$
a related parameter, arterial hemoglobin Oxygen saturation, $SaO_2$
perfusion index, PI
tissue complex permeability
tissue complex permittivity Each of these indicators has normal values which change as the condition of tissue degrades. Studies of the present invention have shown that threshold levels, or decision surfaces, of these parameters or their combinations can be identified as triggers for active intervention by HVPGS between spinal vertebral levels T5 and T12.

Figure 1:
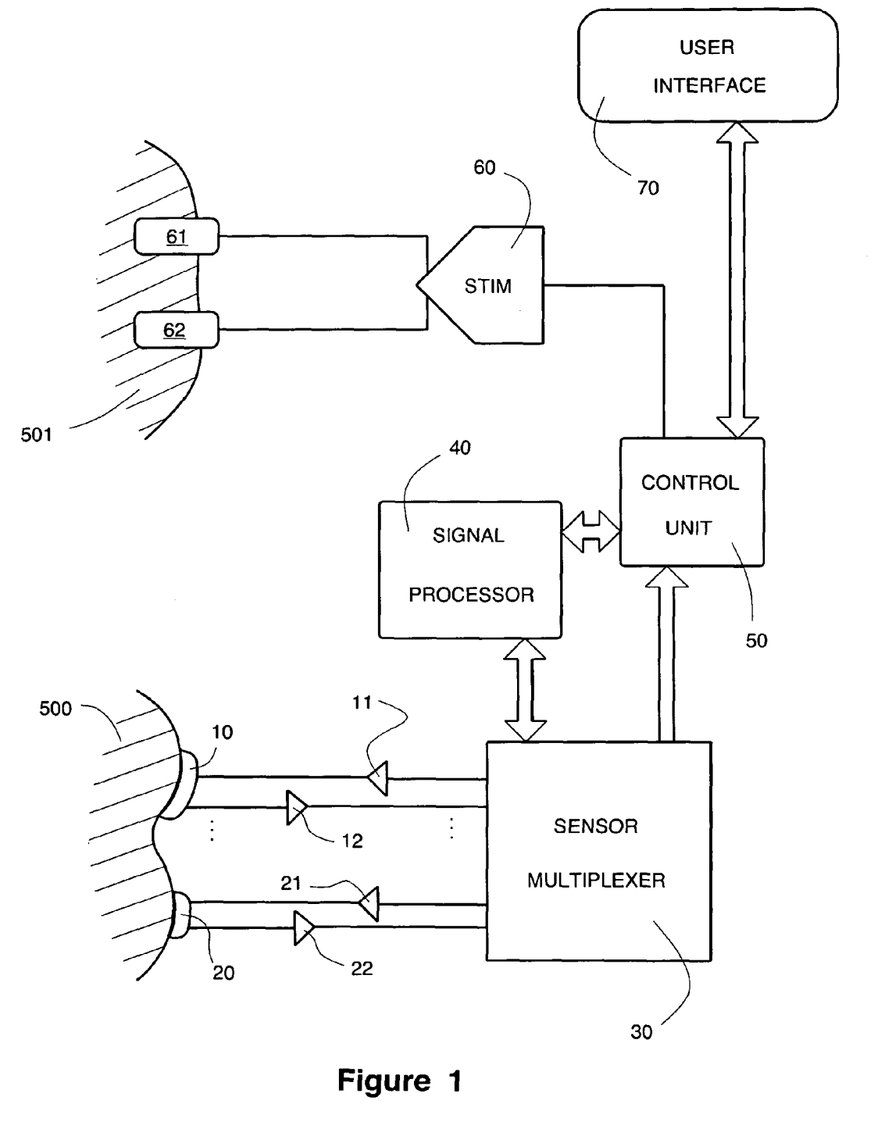
FIG. 1 is a schematic block diagram of the most important components of one embodiment of the invention.

In one embodiment of the present invention, one or more sensors, 10 thru 20, may be used, as illustrated in a system block diagram FIG. 1, to launch a signal, of a type appropriate to the specific sensor, into the tissue at the sacral area, 500, and detect its return. When multiple sensors are used, launched and detected signals are separated by a multiplexer 30. If signal conditioning is necessary, appropriate circuitry, 11,12,21,22, is included for each sensor.

Coordination of signals is accomplished by a control unit 50 which has multiple other functions. These include monitoring signal processor 40 to determine when to stimulate the area of the back 501 between T5 (electrode 61) and T12 (electrode 62), controlling the stimulator 60 to perform appropriate stimulation, and communicating with the user interface 70 to acquire intended operational parameters.

Figure 2A:
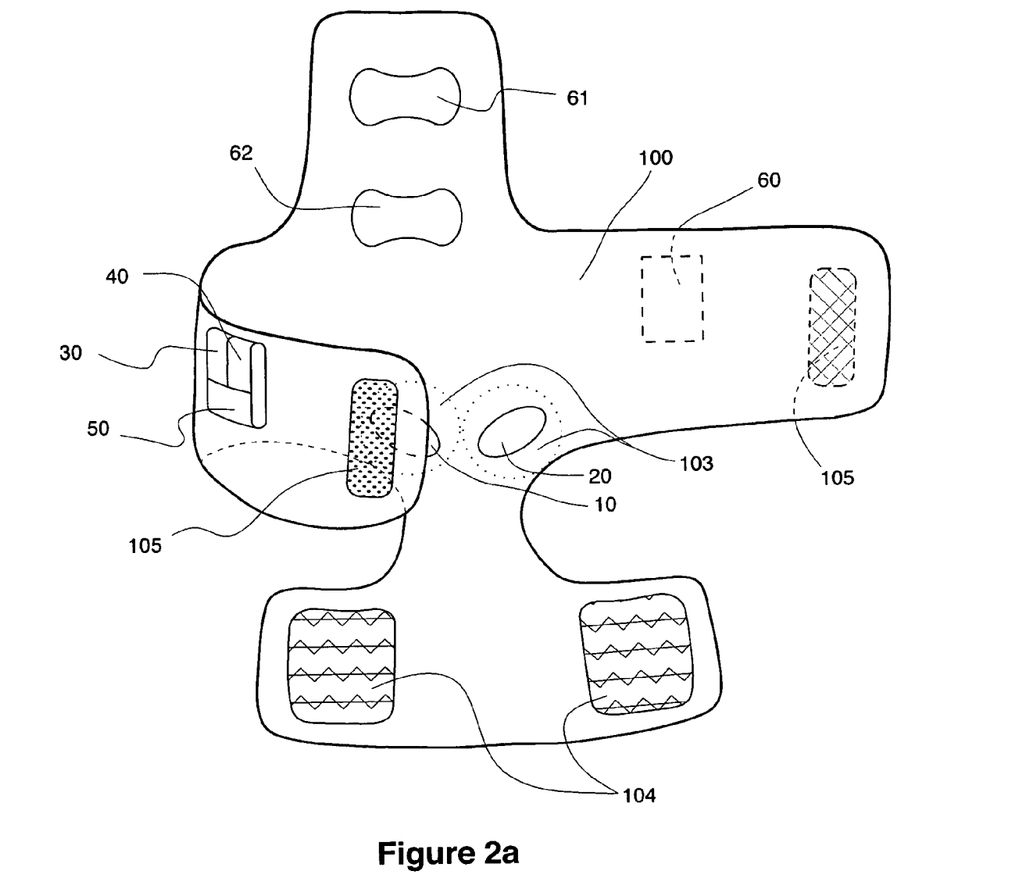
FIG. 2a shows perspective views of one implementition of a wearable vest, in an open, pre-applied orientation, containing sensing areas, stimulation electrodes, and process controller.
Figure 2B:
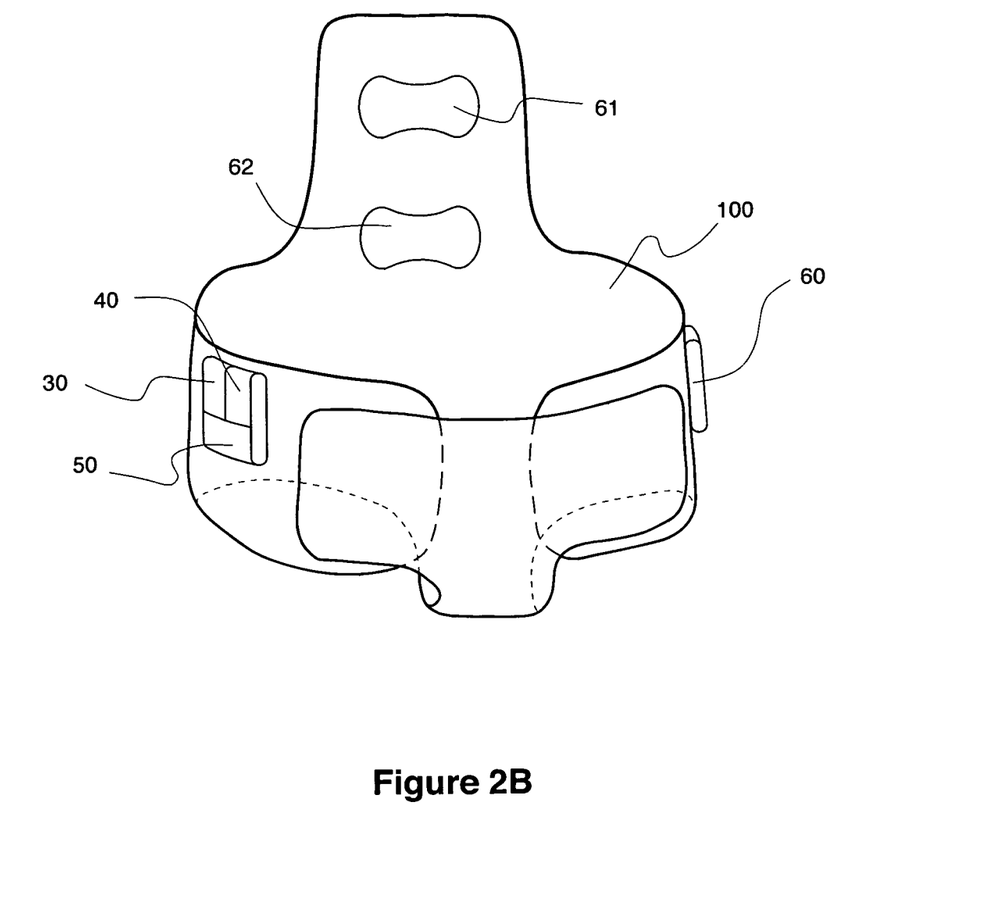
FIG. 2b shows perspective views of the same implementition of a wearable vest as shown in FIG. 2a, but in its orientation while being worn.

A typical embodiment includes a wearable garment 100 shown open for donning, FIG. 2a, or closed as worn, FIG. 2b. This garment contains system electronics (multiplexer 30, signal processor 40, control unit 50, and stimulator 60), sensors 10, 20, stimulator electrodes 101, 102, and closure hooks 105 and closure loops 104. Although tissue ulcers can occur anywhere on the body under appropriate conditions, SCI patients are prone to having breakdown in the tissue over the ischia and lower sacral area. Therefore, these locations 103 are logical locations for sensor location.

Figure 4:
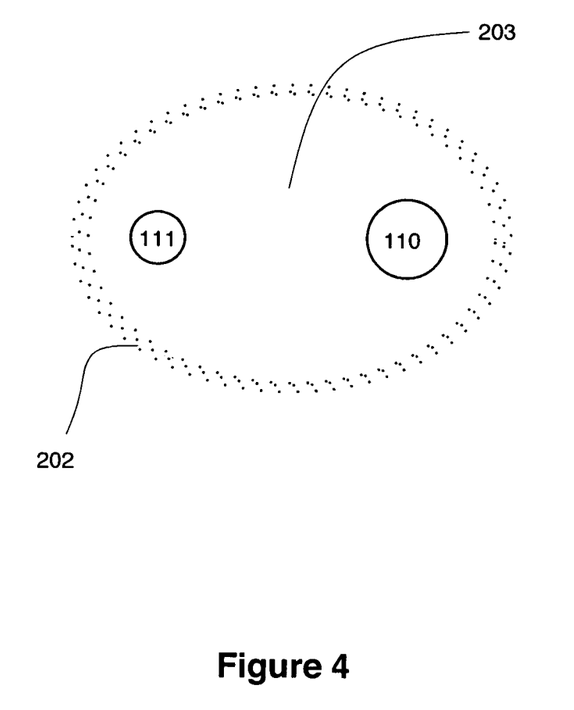
FIG. 4 is a plan view of a single $SpO_2$ unit indicating the approximate area monitored.

Detected signals are operated upon by a signal processing unit 40 which responds to each detector's signal through coordination with the control unit 50. For example in one configuration of the present invention when only one detector is used, and the detector is a single $SpO_2$ unit, FIG. 4, the signal processing unit 40 evaluates the signal received as a small area Oxygen Saturation reading and alarms the control unit 50 to trigger a stimulation event, through stimulation unit 60 and thoracic electrodes 61 and 62, if the signal level is below the predetermined threshold level. In this case when the signal processing unit 40 determines that a small area Oxygen Saturation reading is again above the predetermined threshold level it will signal the control unit 50 to cease stimulation.

Figure 3:
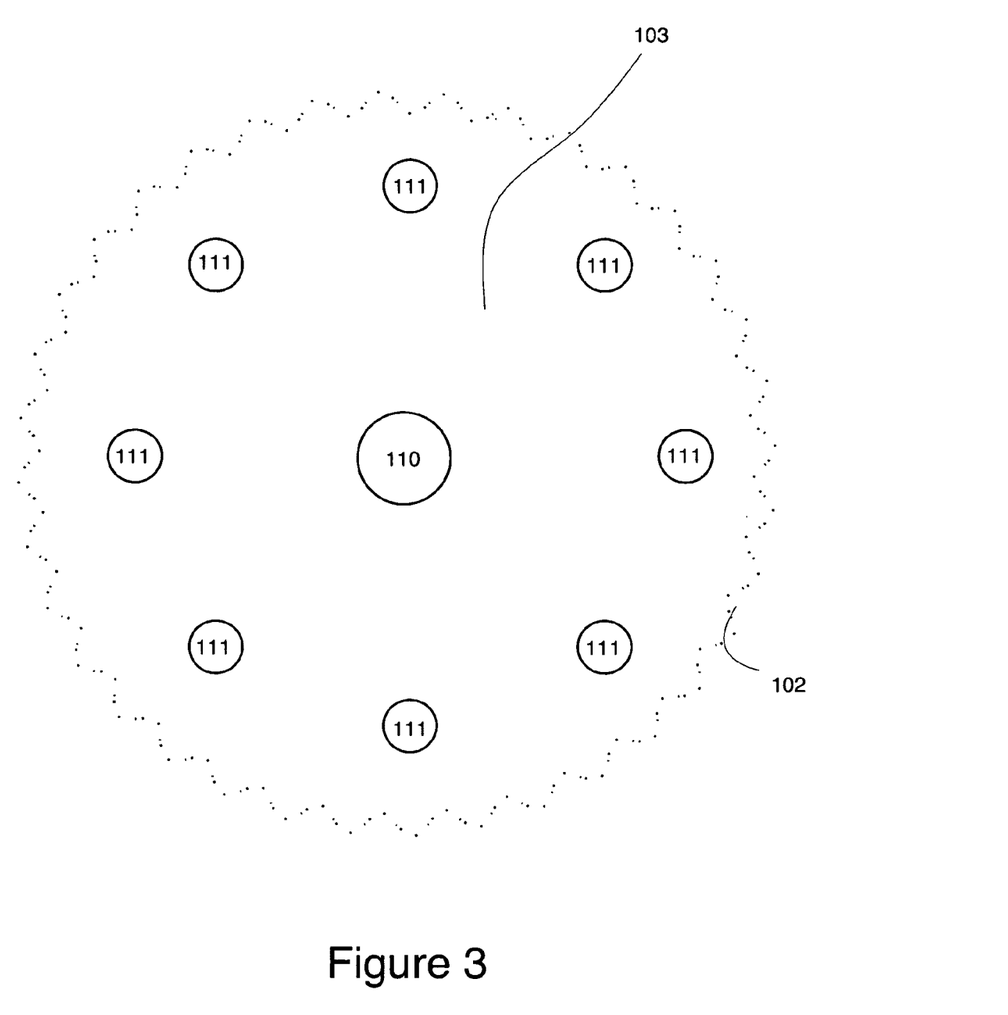
FIG. 3 is a plan view of an $SpO_2$ array sensor indicating the approximate area monitored.

In this same configuration of the present invention, instead of a single $SpO_2$ sensor, the detector may also be an $SpO_2$ array sensor as illustrated in FIG. 3. This sensor is designed to monitor an area 103 with diffuse boundary 102 which may be up to 15 times greater than a single $SpO_2$ unit detection area, 203 with diffuse boundary 202 in FIG. 4. In a process identical to the configuration with a single $SpO_2$, unit, the signal processing unit 40 evaluates the signal received as a large area Oxygen Saturation reading by combining individual detector 111 signals from the array, and alarming the control unit 50 to trigger a stimulation event, through stimulation unit 60 and thoracic electrodes 61 and 62, if the signal level is below the predetermined threshold level. Again when the signal processing unit 40 determines that the large area Oxygen Saturation reading is above the predetermined threshold level it will signal the control unit 50 to cease stimulation.

In another configuration of the present invention a microwave detector is incorporated, either by itself or in conjunction with one or more other detectors. The microwave detector is an antenna which periodically launches an electromagnetic wave into tissue and detects the returned wave. Alternatively, two antennas may be utilized, one to transmit, the other to receive.

What is claimed is:

1. A method for preventing pressure ulcer development involving continuous monitoring of the skin at the sacrum (or other at-risk tissue) for low or declining transcutaneous oxygen tension ($P_{tc}O_2$) levels (such as are found in the spinal cord injured—a group of patients at particularly high risk for development of pressure ulcers), then applying high voltage pulsed galvanic stimulation (HVPGS) at spinal level T5 when $P_{tc}O_2$ levels drop below a set point, wherein application of HVPGS raises the $P_{tc}O_2$ level into the normal range and then automatically terminating HVPGS at that point.

2. A method for preventing pressure ulcer development of claim 1 comprising the steps of:
   (a) placing two conductive electrodes each of approximately 30 $cm^2$ area in contact with the skin positioned on the same side of the spinal column, the active (i.e. negative) electrode in place 2 cm laterally to the spinous process of the T5 vertebrum and the dispersive electrode in place 2 cm laterally to the spinous process of the T12 vertebrum;
   (b) monitoring the state of oxygen tension in the tissues of the sacral or other at-risk area by a $P_{tc}O_2$ sensor for a set point level, approximately 60 mmHg, below which the subject is at high risk of ischemic injury and tissue necrosis;
   (c) activating an electrical stimulator automatically when that set point is reached wherein application of an HVPGS waveform, characterized by a twin-peak monophasic waveform with a fixed pulse duration in the microsecond range (up to 200 µs) and a voltage nominally at 100 volts, gradually increases the measured $P_{tc}O_2$ level up to and beyond the set point as demonstrated in the author's research using patients with spinal cord injury (Mawson et al., 1993);
   (d) terminating HVPGS automatically when the normal $P_{tc}O_2$ range is reached;
   (e) activating the process from step (b) above again in susceptible individuals whose $P_{tc}O_2$ level again begins to drop, wherein the cycle of monitoring and stimulating is repeated.

3. A method for preventing pressure ulcer development involving continuous monitoring of the skin at the sacrum (or other at-risk tissue) for low or declining perfusion index (PI) and hemoglobin oxygen saturation ($SaO_2$) levels (such as are found in the spinal cord injured—a group of patients at particularly high risk for development of pressure ulcers), then applying high voltage pulsed galvanic stimulation (HVPGS) at spinal level T5 when PI and $SaO_2$ levels indicate the tissue is out of the physiological range set point wherein application of HVPGS normalizes vascular tone below the injury bringing PI and $SaO_2$ into the normal range, and then automatically terminating HVPGS at that point.

4. A method for preventing pressure ulcer development of claim 3 comprising the steps of:
   (a) placing two conductive electrodes each of approximately 30 $cm^2$ area in contact with the skin positioned on the same side of the spinal column, the active (i.e. negative) electrode in place 2 cm laterally to the spinous process of the T5 vertebrum and the dispersive electrode in place 2 cm laterally to the spinous process of the T12 vertebrum;
   (b) monitoring the state of PI and $SaO_2$ in the tissues of the sacral or other at-risk area by an $SaO_2$ sensor for a set point level indicating circulatory stasis which, places the subject is at high risk of ischemic injury and tissue necrosis;
   (c) activating an electrical stimulator automatically when that set point is reached wherein application of an HVPGS waveform characterized by a twin-peak monophasic wave form with a fixed pulse duration in the microsecond range (up to 200 µs) and a voltage nominally at 100 volts gradually normalizes vascular tone in the area;
   (d) terminating HVPGS automatically when the normal PI and $SaO_2$ range is reached;
   (e) activating the process from step (b) above again in susceptible individuals whose PI and $SaO_2$ level again begins to drop, wherein the cycle of monitoring and stimulating is repeated.

5. A method for preventing pressure ulcer development involving continuous monitoring of the skin at the sacrum (or other at-risk tissue) for low or declining tissue permittivity at low frequencies with a microwave sensor, then applying high voltage pulsed galvanic stimulation (HVPGS) at spinal level T5 when issue permittivity levels indicate the tissue is out of the physiological range set point wherein application of HVPGS normalizes vascular tone below the injury, bringing issue permittivity into the normal range, and then automatically terminating HVPGS at that point.

6. A method for preventing pressure ulcer development of claim 5 comprising the steps of:

(a) placing two conductive electrodes each of approximately 30 cm² area in contact with the skin positioned on the same side of the spinal column, the active (i.e. negative) electrode in place 2 cm laterally to the spinous process of the T5 vertebrum and the dispersive electrode in place 2 cm laterally to the spinous process of the T12 vertebrum;

(b) monitoring the state of state of tissue permittivity in the tissues of the sacral or other at-risk area periodically by the microwave sensor for a set point level indicating vascular stenosis which places the subject is at high risk of ischemic injury and tissue necrosis;

(c) activating an electrical stimulator automatically when that set point is reached wherein application of an HVPGS waveform characterized by a twin-peak monophasic wave form with a fixed pulse duration in the microsecond range (up to 200 µs) and a voltage nominally at 100 volts gradually normalizes measured tissue permittivity and vascular tone in the area;

(d) terminating HVPGS automatically when the normal tissue permittivity range is reached;

(e) activating the process from step (b) above again in susceptible individuals whose measured tissue permittivity level again begins to drop, wherein the cycle of monitoring and stimulating is repeated.

* * * * *